United States Patent [19]

Barney et al.

[11] Patent Number: 5,455,038
[45] Date of Patent: Oct. 3, 1995

[54] METHOD OF INHIBITING LISTERIA

[75] Inventors: Michael C. Barney, Elm Grove; Lance T. Lusk, Milwaukee; Patrick L. Ting, Brookfield, all of Wis.; David S. Ryder, Libertyville, Ill.

[73] Assignee: Miller Brewing Company, Milwaukee, Wis.

[21] Appl. No.: 308,229

[22] Filed: Sep. 19, 1994

Related U.S. Application Data

[63] Continuation-in-part of Ser. No. 991,613, Dec. 16, 1992, Pat. No. 5,370,863.

[51] Int. Cl.⁶ .............................. A01N 35/06; C12C 3/00
[52] U.S. Cl. ..................... 424/405; 424/409; 424/410; 424/412; 426/335; 426/600
[58] Field of Search ..................... 424/405, 409, 424/410, 412; 426/335, 600

[56] References Cited

U.S. PATENT DOCUMENTS

| | | | |
|---|---|---|---|
| 3,552,975 | 1/1971 | Worden et al. | 426/538 |
| 3,923,897 | 12/1975 | Worden | 568/341 |
| 4,170,638 | 10/1979 | Owades | 424/65 |
| 4,644,084 | 2/1987 | Cowles et al. | 568/341 |
| 4,906,573 | 3/1990 | Barney et al. | 435/243 |
| 5,013,571 | 5/1991 | Hay | 426/600 |
| 5,082,975 | 1/1992 | Todd, Jr. et al. | 568/315 |
| 5,200,227 | 4/1993 | Guzinski et al. | 426/600 |
| 5,286,506 | 2/1994 | Millis et al. | 426/335 |

OTHER PUBLICATIONS

Simpson et al., "Factors affecting antibacterial activity of hop compounds and their derivatives", J. of Applied Bacteriology, vol. 72, No. 4, pp. 327–334 (Apr. 1992).

*Primary Examiner*—John C. Bleutge
*Assistant Examiner*—Robert H. Harrison
*Attorney, Agent, or Firm*—Quarles & Brady

[57] ABSTRACT

A method of inhibiting Listeria in a medium comprises adding to the medium an effective amount of tetrahydroisohumulone or hexahydrocolupulone or mixtures or salts thereof to inhibit any Listeria.

9 Claims, No Drawings

METHOD OF INHIBITING LISTERIA

RELATED CASE

This application is a continuation-in-part of U.S. patent application Ser. No. 07/991,613 filed Dec. 16, 1992, now U.S. Pat. No. 5,370,863.

FIELD OF THE INVENTION

This invention relates to a method of inhibiting food pathogens. More particularly, it relates to a method of inhibiting Listeria.

BACKGROUND OF THE INVENTION

It is known in the brewing industry that some hop acids can inhibit the growth of the microorganisms that can cause spoilage in beer. For example, the Todd Jr. et al. U.S. Pat. No. 5,082,975 discloses that the hop acid, hexahydrolupulone, can inhibit the growth of certain Lactobacillus. In addition, the recently issued Millis et al. U.S. Pat. No. 5,286,506 discloses that solid food products can be protected from food pathogens, including *Listeria monocytogenes*, by incorporating beta-acids, which are extracted from hops, into such food products.

BRIEF SUMMARY OF THE INVENTION

We have now discovered that certain hop acid derivatives are superior as agents for inhibiting Listeria than the beta-acids of the Millis et al. patent. The compounds which we have found to be superior are tetrahydroisohumulone and hexahydrocolupulone.

It is an object of the present invention to disclose a method of inhibiting Listeria employing an inhibitor selected from tetrahydroisohumulone and hexahydrocolupulone.

The novel method of inhibiting Listeria in a medium, such as food or a packaging material for food, basically comprises introducing into the medium a safe amount of a tetrahydroisohumulone or hexahydrocolupulone which is effective to inhibit the Listeria that may be present in or may later enter or come in contact with the medium.

The preferred compound for inhibiting the Listeria is hexahydrocolupulone which surprisingly inhibits Listeria in concentrations of as low as 0.4 ppm to 1.6 ppm.

One advantage of using hexahydrocolupulone is that it is not bitter in flavor and should have little organoleptic effect on foods.

The advantages of using tetrahydroisohumulone are that it is commercially available, as opposed to the Millis et al. products, and it is currently cheaper than hexahydrocolupulone.

It will be apparent to those skilled in the art that the above described and additional objects and advantages may be obtained by the practice of the present invention.

DESCRIPTION OF THE PREFERRED EMBODIMENTS

The preferred method of the present invention comprises incorporating a safe and effective amount of an inhibitor selected from hexahydrocolupulone, tetrahydroisohumulone mixtures thereof and the salts thereof into a medium to inhibit Listeria growth.

"Safe and effective amount" as used herein means an amount of the inhibitor which is enough to provide the desired inhibition, but not so high as to cause undesirable other properties, such as an unacceptable taste. The safe and effective amount will vary with the particular inhibitor chosen, and the taste or flavoring of the particular food to which the inhibitor is to be added or which is to be wrapped in the packaging materials containing the inhibitor.

Other inhibitors and agents, such as anti-mold agents, which do not interfere with the desired inhibition of Listeria also can optionally be added in the method of this invention.

The term "medium" as used herein is intended to include both solid and liquid foods, as well as packaging materials from which the inhibitor can be released to inhibit organisms on the surface of foods.

The term "tetrahydroisohumulone" as used herein includes a mixture of tetrahydroisohumulone, tetrahydroisoadhumulone and tetrahydroisocohumulone. The mixture is commercially available or can be prepared for example by use of the method of the Cowles et al. U.S. Pat. No. 4,644,084. The tetrahydroisohumulone is effective in inhibiting Listeria when used in concentrations of 8 ppm to 16 ppm in a solid or liquid medium.

The hexahydrocolupulone is a known compound which can be made by the chemical hydrogenation of colupulone with platinum (IV) oxide as the catalyst as described by W. Riedl, J. Nickl, Ber, 89 (1956) p. 1863 or J. F. Carson, J. Am. Chem. Soc., 73 (1951) p. 1850. The hexahydrocolupulone is effective in inhibiting Listeria when used in concentrations of about 0.4 ppm to about 1.6 ppm.

The practice of the present invention is further illustrated by the examples which follow:

EXAMPLE 1

Minimal Inhibitory Concentration (MIC) Assay

The basic assay was performed by serially diluting the inhibitors using a two-fold dilution series in a nutrient broth. The dilutions provided inhibitor concentrations in the range of 1000 ppm to 0.1 ppm. The nutrient broth used was Difco Tryptic Soy Broth (pH 6.7) for the Listeria species. All dilution series were inoculated with approximately $10^4$ freshly cultured (using the same medium) cells per 5 ml of test assay broth. In each assay an inoculated sample of the broth without any inhibitor addition was used as a positive control, and an uninoculated tube of broth served as a negative control.

Results and Discussion

The results of the studies are summarized in Table I which gives the data from testing the effectiveness of the tetrahydroisohumulone and hexahydrocolupulone in inhibiting *Listeria monocytogenes*. As the data show tetrahydroisohumulone inhibited the test strain at a concentration between 8 and 16 ppm in Tryptic Soy Broth. The compound, hexahydrocolupulone (HHCL), surprisingly inhibited the Listeria test strain at very low concentrations near 0.4 ppm.

Table II presents the data from an expanded experiment to test the effectiveness of HHCL against eight different Listeria strains. HHCL was very effective at inhibiting all of the strains tested at concentrations between 0.4 and 1.6 ppm.

TABLE I

The Minimal Inhibitory Concentrations of
Tetrahydroisohumulone and Hexahydrocolupulone on *Listeria monocytogenes* Strain Scott A

| Tube Number | Hop Acid Concentration | Growth (Turbidity/Sediment)* |
|---|---|---|
| *Tetrahydroisohumulone:* | | |
| 1 | 1000 ppm | − |
| 2 | 500 ppm | − |
| 3 | 250 ppm | − |
| 4 | 125 ppm | − |
| 5 | 63 ppm | − |
| 6 | 31 ppm | − |
| 7 | 16 ppm | − |
| 8 | 8 ppm | + |
| 9 | 4 ppm | + |
| 10 | 2 ppm | + |
| 11 | 1 ppm | + |
| 12 (+ control) | 0 ppm | + |
| *Hexahydrocolupulone:* | | |
| 1 | 100.0 ppm | − |
| 2 | 50.0 ppm | − |
| 3 | 25.0 ppm | − |
| 4 | 12.5 ppm | − |
| 5 | 6.3 ppm | − |
| 6 | 3.1 ppm | − |
| 7 | 1.6 ppm | − |
| 8 | 0.8 ppm | − |
| 9 | 0.4 ppm | +/− |
| 10 | 0.2 ppm | + |
| 11 | 0.1 ppm | + |
| 12 (+ control) | 0 ppm | + |

*Growth (Turbidity/Sediment) - observed in tubes of Tryptic Soy Broth after 3 days incubation at 35° C. - "±" = good growth, "+/−" = faint growth, "−" = no growth

TABLE II

The Minimal Inhibitory Concentrations of
Hexahydrocolupulone on Eight Listeria Strains

| Tube No. | Hop Acid Conc. | *Listeria monocytogenes* strains | | | | | | *L. innocua* | *L. seeligeri* |
|---|---|---|---|---|---|---|---|---|---|
| | | OM3 | OM4 | OM5 | OM6 | V7 | Scott A | | |
| 1 | 100.0 ppm | − | − | − | − | − | − | − | − |
| 2 | 50.0 ppm | − | − | − | − | − | − | − | − |
| 3 | 25.0 ppm | − | − | − | − | − | − | − | − |
| 4 | 12.5 ppm | − | − | − | − | − | − | − | − |
| 5 | 6.3 ppm | − | − | − | − | − | − | − | − |
| 6 | 3.1 ppm | − | − | − | − | − | − | − | − |
| 7 | 1.6 ppm | − | − | − | +/− | − | − | − | − |
| 8 | 0.8 ppm | − | − | − | + | + | − | + | − |
| 9 | 0.4 ppm | + | + | + | + | + | +/− | + | +/− |
| 10 | 0.2 ppm | + | + | + | + | + | + | + | + |
| 11 | 0.1 ppm | + | + | + | + | + | + | + | + |
| 12 | 0 ppm | + | + | + | + | + | + | + | + |

*Growth (Turbidity/Sediment) - observed in tubes of Tryptic Soy Broth after 3 days incubation at 35° C. - "+" = good growth, "+/−" = faint growth, "−" = no growth The salts of the inhibitors which can be used in the method of the present invention are preferably the sodium and potassium salts. They are easily prepared by conventional salt forming methods and more soluble than hexahydrocolupulone or tetrahydroisohumulone.

The inhibitors can be incorporated directly into foods or incorporated into a medium, such as a packaging material, which, when in contact with the surface of the food where Listeria and other organisms commonly grow, will release the inhibitor.

Representative of products (media) which can be protected by the method of the present invention are the following:

A. Solids cheese sausage processed meat beans turkey chicken vegetables

B. Liquids milk salad dressings sauces.

It will be readily apparent to those skilled in the art that a number of modifications and changes can be made without departing from the spirit and scope of the invention. Therefore, it is intended that the invention be limited only by the claims.

We claim:

1. A method of inhibiting Listeria which comprises contacting said Listeria with an effective amount of a compound selected from the group consisting of hexahydrocolupulone, tetrahydroisohumulone, salt thereof and mixtures thereof to inhibit said Listeria.

2. A method of inhibiting Listeria in a medium which comprises adding to the medium an effective amount of a compound selected from the group consisting of hexahydrocolupulone, tetrahydroisohumulone, salts thereof and mixtures thereof to inhibit any Listeria which may be present in the medium.

3. A method of claim 2 in which the medium is a solid food.

4. A method of claim 2 in which the medium is a liquid food.

5. A method of claim 2 in which the medium is processed meat.

6. A method of claim 2 in which the medium is a poultry meat.

7. A method of claim 2 in which the medium is a packaging material.

8. A method of claim 2 in which the compound is hexahydrocolupulone.

9. A method of claim 2 in which the compound is tetrahydroisohumulone.

* * * * *